US010729565B2

(12) United States Patent
Whiteside (10) Patent No.: US 10,729,565 B2
(45) Date of Patent: Aug. 4, 2020

(54) POST-OPERATIVE RESIDUAL LIMB SUPPORT ASSEMBLY

(71) Applicant: Hanger, Inc., Austin, TX (US)

(72) Inventor: Stacey A. Whiteside, Chandler, AZ (US)

(73) Assignee: Hanger, Inc., Austin, TX (US)

( * ) Notice: Subject to any disclaimer, the term of this patent is extended or adjusted under 35 U.S.C. 154(b) by 0 days.

(21) Appl. No.: 16/051,019

(22) Filed: Jul. 31, 2018

(65) Prior Publication Data

US 2018/0333278 A1 Nov. 22, 2018

Related U.S. Application Data

(63) Continuation-in-part of application No. 15/857,513, filed on Dec. 28, 2017.

(60) Provisional application No. 62/440,204, filed on Dec. 29, 2016.

(51) Int. Cl.
| | |
|---|---|
| *A61F 2/78* | (2006.01) |
| *A61F 2/76* | (2006.01) |
| *A61F 2/60* | (2006.01) |
| *A61F 2/50* | (2006.01) |
| *A61F 2/30* | (2006.01) |

(52) U.S. Cl.
CPC .............. *A61F 2/78* (2013.01); *A61F 2/60* (2013.01); *A61F 2/76* (2013.01); *A61F 2002/30433* (2013.01); *A61F 2002/5026* (2013.01); *A61F 2002/5081* (2013.01); *A61F 2002/7862* (2013.01)

(58) Field of Classification Search
CPC .. A61F 2/78; A61F 2/7812; A61F 2/58; A61F 2/582; A61F 2/80
See application file for complete search history.

(56) References Cited

U.S. PATENT DOCUMENTS

| | | | |
|---|---|---|---|
| 2013/0338794 A1* | 12/2013 | Whiteside | A61F 2/80 623/36 |
| 2014/0371646 A1* | 12/2014 | Kozersky | A61F 5/026 602/19 |
| 2018/0021153 A1* | 1/2018 | Hurley | A61F 2/80 623/36 |
| 2018/0185175 A1 | 7/2018 | Whiteside et al. | |

* cited by examiner

*Primary Examiner* — Bruce E Snow
(74) *Attorney, Agent, or Firm* — Foley & Lardner LLP (57) ABSTRACT

An upper extremity post-operative residual limb support assembly includes an upper frame; a lower frame adjustably coupled to the upper frame; a liner coupled to the upper frame and the lower frame, the liner including: a first liner portion configured to be positioned adjacent the upper frame and extend at least partially about an arm of a user; and a second liner portion configured to be positioned adjacent the lower frame, the second liner portion including a closed end configured to receive a distal end of a residual portion of the arm.

19 Claims, 6 Drawing Sheets

POST-OPERATIVE RESIDUAL LIMB SUPPORT ASSEMBLY

CROSS-REFERENCE TO RELATED APPLICATIONS

This application is a continuation-in-part of U.S. application Ser. No. 15/857,513, filed Dec. 28, 2017, which claims the benefit of U.S. Provisional Application No. 62/440,204, filed Dec. 29, 2016. The entire disclosures of these applications are incorporated herein by reference.

BACKGROUND

The present disclosure relates generally to post-operative residual limb supports. More specifically, the present disclosure relates to post-operative residual limb supports that may provide improved fit, protection, comfort and function for users having above-the-elbow (AE), also known as transradial, and/or below-the-elbow (BE), also known as trans-radial, upper extremity amputations.

SUMMARY

One embodiment relates to an upper extremity post-operative residual limb support assembly. The assembly includes an upper frame; a lower frame adjustably coupled to the upper frame; and a liner coupled to the upper frame and the lower frame, the liner including a first liner portion configured to be positioned adjacent the upper frame and extend at least partially about an arm of a user, and a second liner portion configured to be positioned adjacent the lower frame, the second liner portion including a closed end configured to receive a distal end of a residual portion of the arm.

Another embodiment relates to a post-operative support assembly. The assembly includes a frame assembly including an upper cuff portion configured to extend at least partially about an arm, at least one elongated member configured to extend along a portion of the arm, and a lower cup portion coupled to the upper cuff portion by the at least one elongated member and configured to extend about a distal end of a residual portion of the arm; and a liner coupled to the frame assembly and positioned between the frame assembly and the residual portion of the arm , the liner configured to at least partially conform to the residual portion of the arm.

Another embodiment relates to a post-operative support assembly. The assembly includes an upper frame including a curved cuff portion and an upper elongated member; a lower frame including a curved cup portion and a lower elongated member adjustably coupled to the upper elongated member to enable adjustment of a length between the curved cuff portion and the curved cup portion; an upper liner coupled to an inner surface of the upper frame; a lower liner coupled to an inner surface of the lower frame and including an open top portion and a closed bottom portion, wherein the closed bottom portion is configured to receive a distal end of a residual portion of an arm; and a retention strap extending about the lower frame and the lower liner to secure the lower frame and the lower liner about the residual portion of the arm.

This summary is illustrative only and is not intended to be in any way limiting.

BRIEF DESCRIPTION OF THE FIGURES

The disclosure will become more fully understood from the following detailed description, taken in conjunction with the accompanying figures, wherein like reference numerals refer to like elements, in which.

DETAILED DESCRIPTION

Before turning to the figures, which illustrate certain exemplary embodiments in detail, it should be understood that the present disclosure is not limited to the details or methodology set forth in the description or illustrated in the figures. It should also be understood that the terminology used herein is for the purpose of description only and should not be regarded as limiting.

Referring generally to the figures, a post-operative residual limb support (e.g., a support assembly) is shown according to various embodiments. The support assembly may be used immediately/shortly after amputation of a portion of a limb, such as a portion of a patient's arm (e.g., such as in the case of an AE amputation or a BE amputation). After the amputation procedure, there is often a period of time prior to a patient being fitted with a permanent prosthesis. It is often desirable to provide proper support and protection for the residual limb to protect the patient from injury, to permit the residual limb to heal properly, and to prepare the residual limb for a permanent prosthesis.

Referring now to FIGS. 1-9, a support assembly 10 is shown according to one embodiment. Support assembly 10 may in some embodiments be usable with above-elbow (AE) amputations, although support assembly 10 may find uses in other applications. Support assembly 10 includes a frame assembly 12, an upper liner 14, a lower liner 16, a strap 18 (e.g., an outer wrap, etc.), and a harness assembly 22 (e.g., a retention strap, etc.). The upper and lower liners 16, 18 are fastened to the frame assembly 12 using one or more liner fasteners 20 (e.g., screws, rivets, other mechanical fastening components, etc.).

Frame assembly 12 includes an upper frame 24, a lower frame 26, and one or more fasteners 28. Upper frame 24 may be coupled to lower frame 26 using fasteners 28 (e.g., screws/nuts, rivets, other mechanical fastening components, etc.). Frame assembly 12 is generally shaped to receive upper and lower liners 14, 16 and conform to the shape of the upper arm and residual limb portion of a user post-amputation (e.g., after an AE amputation procedure). In one embodiment, the structural frame components are made of a rigid or semi-rigid material, such as a moldable plastic (e.g., polyvinyl chloride, acrylic, acrylic-polyvinyl chloride, etc.), a metal (e.g., aluminum, steel, stainless steel, etc.), three-dimensional printable material (e.g., plastic or metal, etc.), thermosetting plastics or polymers (e.g., epoxy, polyester fiberglass, polyurethane, polyimides, melamine resin, etc.), or the like.

Upper frame 24 includes an elongated portion 30 and a cuff portion 32. Elongated portion 30 is configured to extend along an outer portion of an upper arm of a user. Cuff portion 32 extends generally transversely relative to elongated portion 30, and may be curved to conform to the shape of the upper arm or shoulder area of a user.

Lower frame 26 includes an elongated portion 34 and a cuff or cup portion 36. Elongated portion 34 is configured to extend along an outer portion of an upper arm of a user. Elongated portion 34 may include a slot 38 (e.g., an elongated recess or channel) extending along a portion of lower frame 26. In some embodiments, fasteners 28 extend through an aperture in elongated portion 30 of upper frame 24 and into slot 38 in elongated portion 34 of lower frame 26 to enable sliding movement of upper frame 24 relative to lower frame 26, and length-adjustment of frame assembly 12 and support assembly 10. Fastener 28 may include, for example, a threaded screw and nut (as similarly shown in FIG. 12) that enable selective tightening and loosening of fastener 28. Fastener 28 may be tightened to secure frame assembly 12 and support assembly 10 in a desired position. As such, support assembly 10 provides a universal fit feature such that support assembly 10 can accommodate different length arms and residual limbs resulting from different users and different amputation procedures.

Upper liner 14 is received by cuff portion 32 of upper frame 24 and secured in place using one or more fasteners 20. Upper liner 14 may extend slightly beyond the periphery of cuff portion 32 to minimize contact between cuff portion 32 and a user's arm and to provide a more comfortable fit. Upper liner 14 may be made of a flexible, deformable material such that upper liner 14 conforms to the shape of cuff portion 32.

Lower liner 16 includes a strap fastener 40, a bottom portion 42, and one or more slits 44. Strap fastener 40 is configured to couple to strap 18 to maintain strap 18 in a desired position. Strap fastener 40 may be or include a hook and loop fastener, a mechanical fastener (e.g., a button, clip, threaded fastener, a snap fit fastener, etc.), or any other suitable fastener. Lower liner 16 is in one embodiment generally cylindrical in shape with an open top and a closed bottom.

Figure 6:
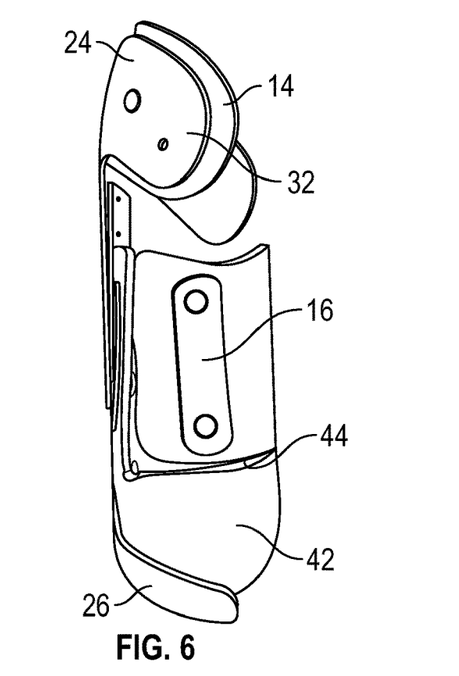
FIG. 6 is a side view of a portion of the support assembly of FIG. 1 according to one embodiment.
Figure 7:
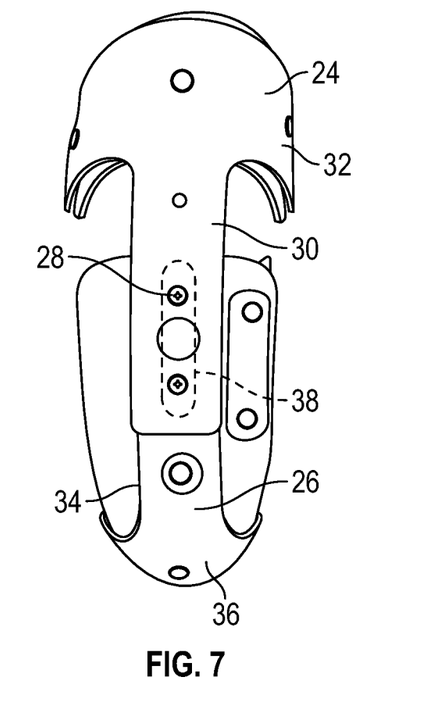
FIG. 7 is a rear view of a portion of the support assembly of FIG. 1 according to one embodiment.
Figure 8:
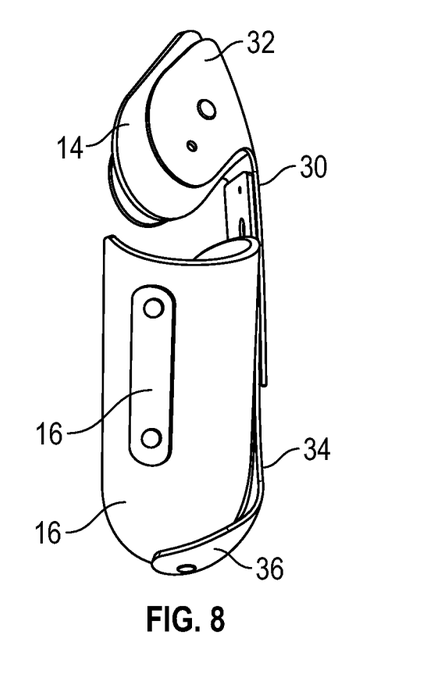
FIG. 8 is another side view of a portion of the support assembly of FIG. 1 according to one embodiment.
Figure 9:
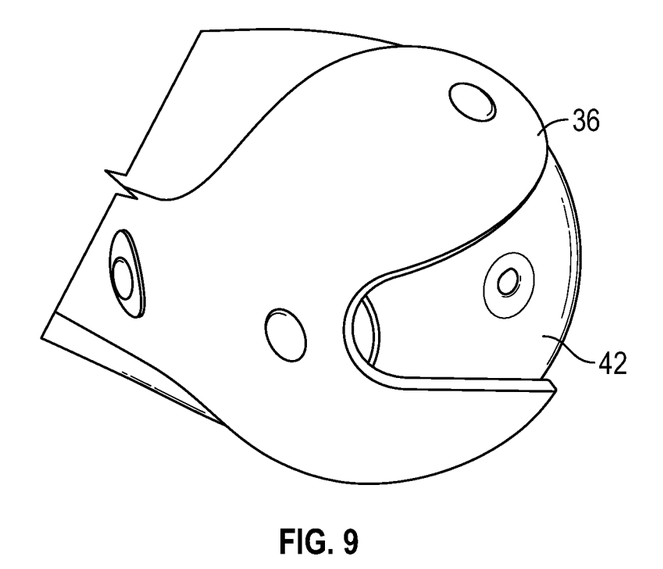
FIG. 9 is a bottom view of a portion of the support assembly of FIG. 1 according to one embodiment.

Referring to FIG. 6, in some embodiments lower liner 16 includes one or more slits 44 (e.g., cuts, breaks, etc.). Slits 44 are configured to facilitate placement of support assembly 10 onto a user's arm. Slits 44 may extend longitudinally (e.g., along a length of an arm), transversely, or at other orientations. Slits 44 may form a flap portion that can be flexed to facilitate insertion and removal of a residual limb from lower liner 16.

Upper and lower liners 14, 16 may be made of any suitable material, including formable foam, plastic, or rubber materials, such as ethylene-vinyl acetate foam, thermoplastic closed-cell foam, polyethylene foam, polyethylene, 3D printable material, thermoset foams, thermo-formable foams, memory foams, closed cell foam, open cell foam, and the like.

Strap 18 is in one embodiment an elongated portion of flexible and/or elastic material configured to wrap about frame assembly 12 and lower liner 16. Strap 18 may in some embodiments provide a compressive force to the residual limb. Strap 18 may be made of any suitable material, and may include opposite ends that include fasteners such as hook and loop fasteners, etc. Alternatively, strap 18 may be a continuous band of material.

Figure 1:
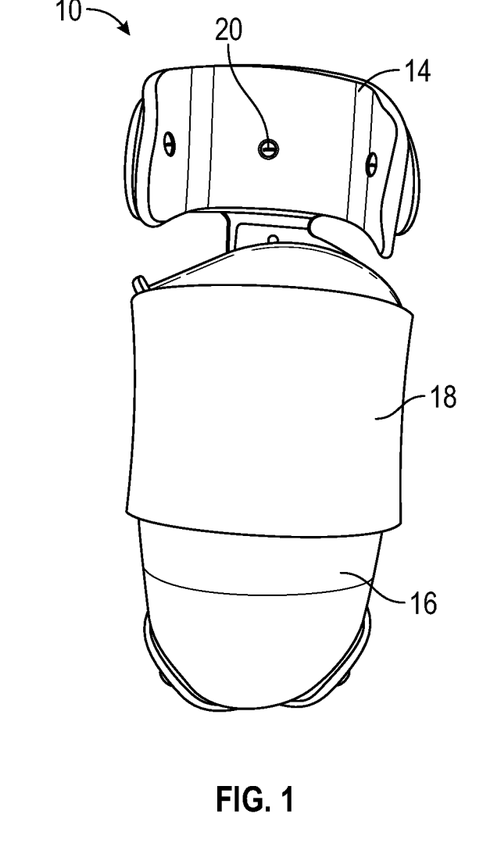
FIG. 1 is a front view of a support assembly according to one embodiment.
Figure 2:
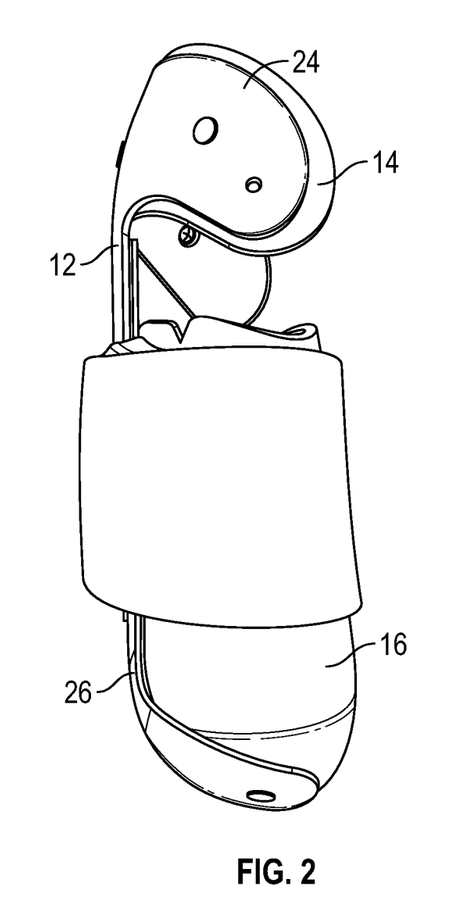
FIG. 2 is a side view of the support assembly of FIG. 1 according to one embodiment.
Figure 3:
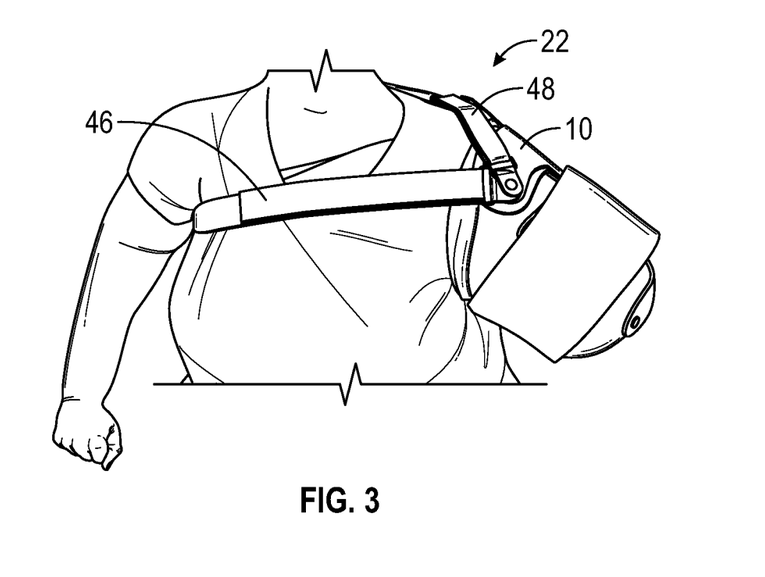
FIG. 3 is a front view of a support assembly fitted on a patient according to one embodiment.
Figure 4:
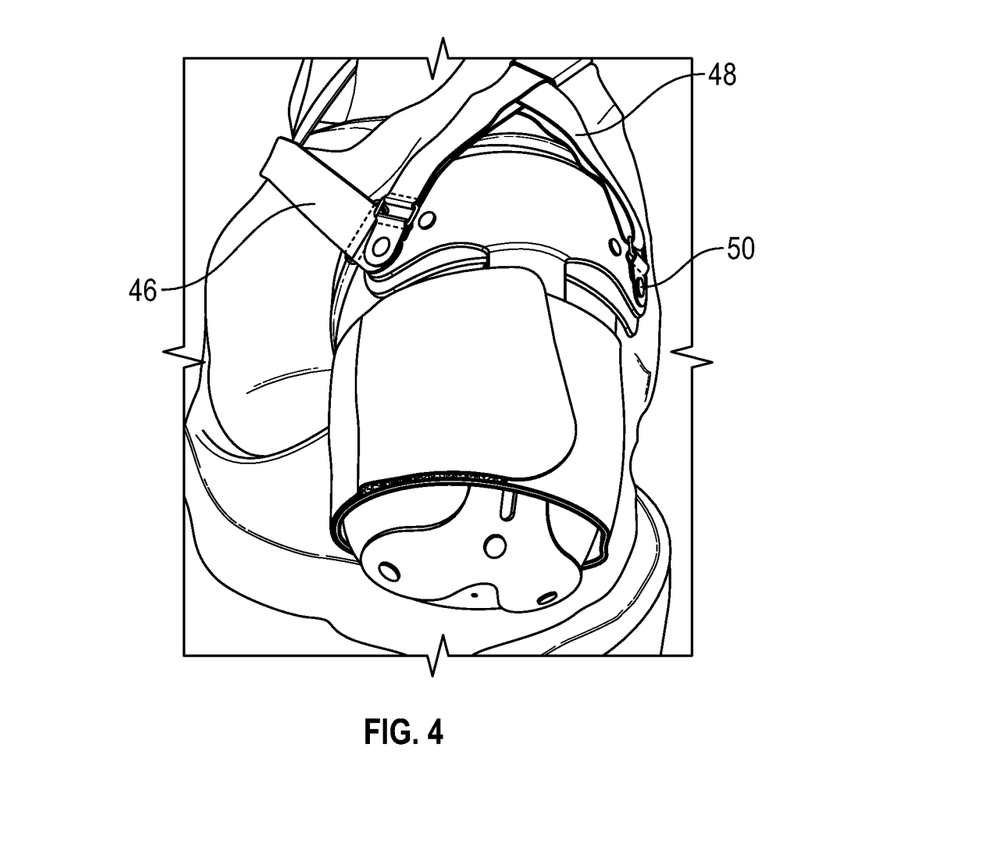
FIG. 4 is a side view of a support assembly fitted on a patient according to one embodiment.
Figure 5:
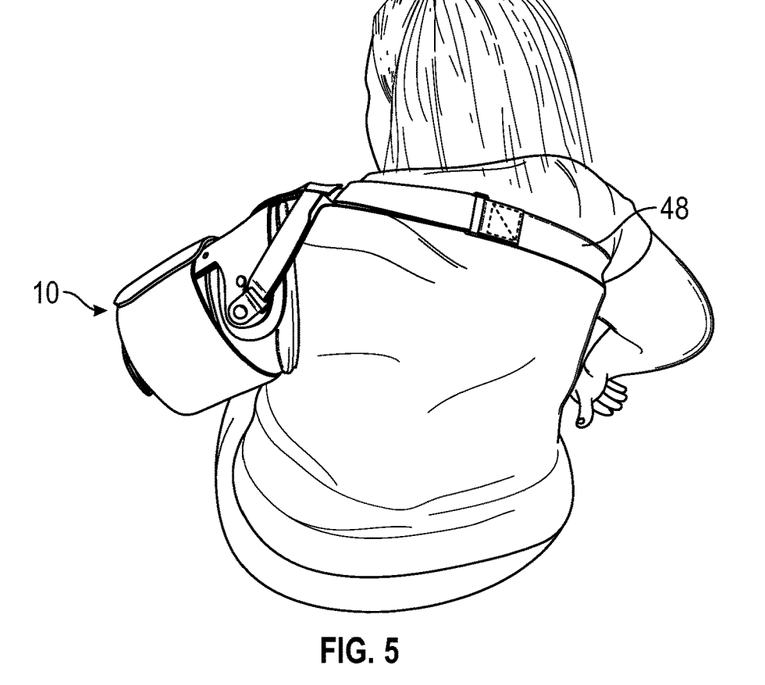
FIG. 5 is a rear view of a support assembly fitted on a patient according to one embodiment.

Harness assembly 22 includes a front strap portion 46 and a rear strap portion 48, and is fastened to frame assembly 12 by one or more harness fasteners 50. As shown in FIGS. 3-5, in one embodiment, front strap portion 46 extends from an upper portion of frame assembly 12 (e.g., cuff portion 32 of upper frame 24) and around a front upper torso or chest area of a user. Similarly, rear strap portion 48 may extend from an upper portion of frame assembly 12 and around a rear supper torso or back area of a user. Front strap portion 46 and rear strap portion 48 may form a continuous strap that extends around the user. In some embodiments, one or both ends of the front and rear strap portions 46, 48 may be Y-shaped to enable attachment to the opposing ends of cuff portion 32 of upper frame 24. Further, the strap portions may be adjustable in length to accommodate variations in users, residual limbs, etc.

In use, support assembly 10 may be provided without strap 18 or harness assembly 22 fully installed (although one or both of strap 18 and harness assembly 22 may be loosely attached, e.g., by a single end or in a loosened state). A user places a residual limb (e.g., post AE amputation) within bottom portion 42 of lower liner 16, which forms a lower cup or dome shape to accommodate the distal end of the residual limb. A portion of lower liner 16 may be flexed back dues to slits 44, to facilitate insertion of the residual limb. Once the residual limb is properly seated within lower liner 16, strap 18 may be secured about frame assembly 12 and lower liner 16. After strap 18 is properly secured, harness assembly 22 may be positioned and tightened about the torso/chest/back of the user.

In some embodiments, support assembly 10 is reversible such that support assembly is usable on either a right or left upper extremity. For example, FIGS. 3-5 illustrate support assembly used with a left residual limb. For use with a right residual limb, harness assembly 22 can be reversed (e.g., by reversing the attachment points) and the support assembly 10 can otherwise be fitted as on the left residual limb. Providing a universal support assembly avoids the need to produce different support assemblies to accommodate left and right limbs.

Figure 10:
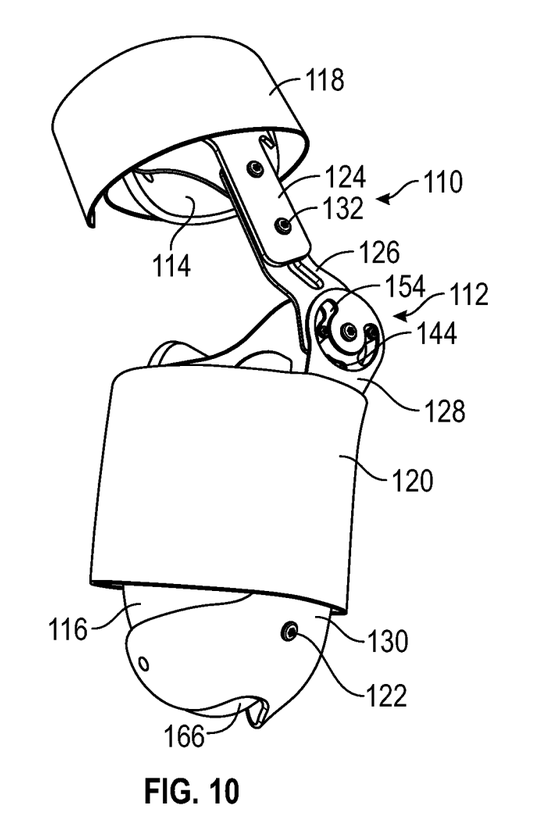
FIG. 10 is a side view of a support assembly according to another embodiment.
Figure 11:
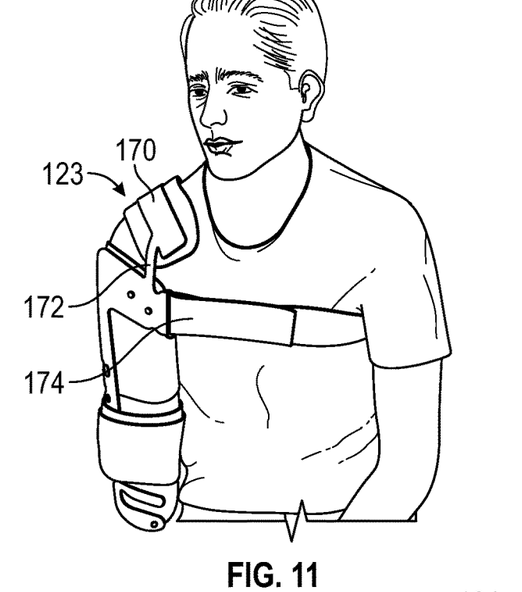
FIG. 11 is a side view of a support assembly fitted on a patient according to one embodiment.
Figure 12:
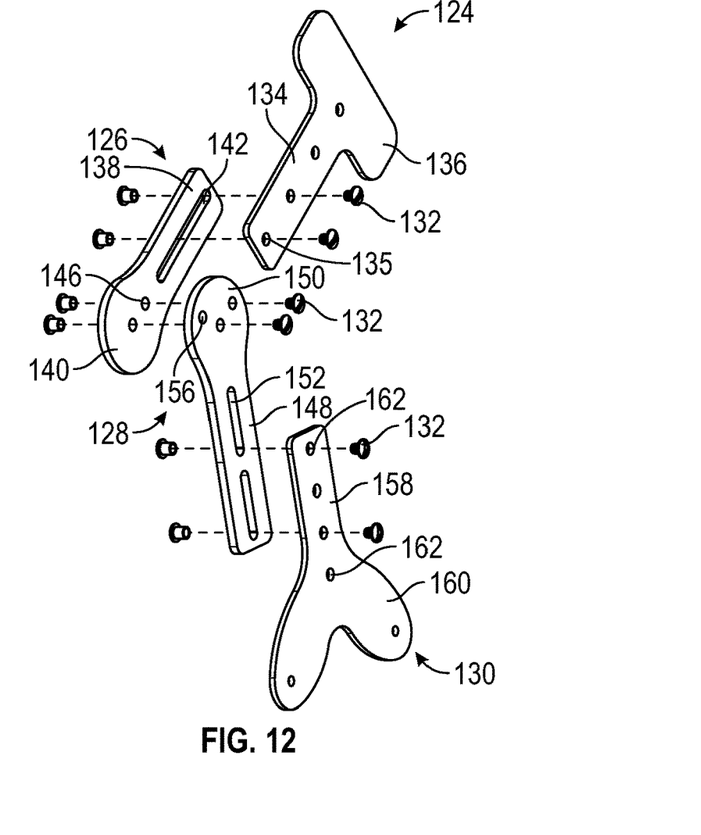
FIG. 12 is an exploded view of component parts for a support assembly according to one embodiment.

Referring now to FIGS. 10-12, a support assembly 110 is shown according to an alternative embodiment. Support assembly 110 shares many features with support assembly 10, except that while support assembly 10 may find application primarily in connection with AE amputations, support assembly 110 may find application primarily in connection with BE amputations. As such, certain features of support assembly 110 are modified relative to support assembly 10 to accommodate a longer residual limb, an elbow, and the like.

In one embodiment, support assembly 110 includes a frame assembly 112, an upper liner 114, a lower liner 116, an upper strap 118, a lower strap 120, and a harness assembly 123. One or more liner fasteners 122 may be used to fasten upper and lower liners 114, 116 to frame assembly 112.

Frame assembly 112 includes an upper support portion 124, an upper hinge portion 126, a lower hinge portion 128, a lower support portion 130, and fasteners 132 that couple the various components of frame assembly 112 together. Upper support portion 124 and upper hinge portion 126 collectively form an upper frame, and lower hinge portion 128 and lower support portion 130 collectively form a lower frame that is fixedly or adjustably coupled to the upper frame. Frame assembly 112 is generally shaped to receive upper and lower liners 114,116 and conform to the shape of the upper arm of a user post-amputation (e.g., after a BE amputation procedure). The structural components of frame assembly 112 may be made of the same materials as frame assembly 12.

Upper support portion 124 includes an elongated portion 134 and a cuff portion 136. Elongated portion 134 is configured to extend along an outer portion of an upper arm of a user. Cuff portion 136 extends generally transversely relative to elongated portion 134, and may be curved to conform to the shape of the upper arm or shoulder area of a user.

Upper hinge portion 126 includes an elongated portion 138 and an upper hinge plate portion 140. An elongated slot 142 may extend along a portion of the length of upper hinge portion 126, and one or more apertures 146 may be provided on elongated portion 138 and/or upper hinge plate portion 140. Further, a circumferential slot 144 (see FIG. 10) may provide rotational adjustment features for frame assembly 112.

Upper support portion 124 is adjustably coupled to upper hinge portion 126 to form the upper frame and provide length adjustment features for the upper frame. As shown in FIG. 12, fasteners 132 extend through apertures 135 in upper support portion 124 and into elongated slot 142 in upper hinge portion 126. In this way, the overall length of the upper frame may be adjusted by sliding upper support portion 124 relative to upper hinge portion 126, and securing the components in a desired position (e.g., to accommodate an upper arm length of a user).

Lower hinge portion 128 includes an elongated portion 148 and a lower hinge plate portion 150. An elongated slot 152 may extend along a portion of the length of lower hinge portion 128, and one or more apertures 156 may be provided on elongated portion 138 and/or lower hinge plate portion 150. Further, a circumferential slot 154 (see FIG. 10) may provide rotational adjustment features for frame assembly 112.

Lower support portion 130 includes an elongated portion 158 and a cuff or cup portion 160. Elongated portion 158 is configured to extend along an outer portion of a lower arm of a user. Elongated portion 158 may include one or more apertures 162. Lower support portion 130 is adjustably coupled to lower hinge portion 128 to form the lower frame and provide length adjustment features for the lower frame. As shown in FIG. 12, fasteners 132 extend through apertures 162 in lower support portion 130 and into elongated slot 152 in lower hinge portion 128. As shown in FIG. 12 a single slot (as with upper hinge portion 126) or multiple slots (as with lower hinge portion 128) may be utilized to provide length adjustment features. In this way, the overall length of the lower frame may be adjusted by sliding lower support portion 130 relative to lower hinge portion 128, and securing the components in a desired position (e.g., to accommodate a residual limb length of a user). It should be noted that FIG. 12 shows the various components as being flat (e.g., prior to being formed with the contours of the cuff portion, cup portion, etc.). Support assembly 110 provides a universal fit feature such that support assembly 110 can accommodate different length residual limbs resulting from different users and different amputation procedures.

To accommodate elbow movement, the upper frame is adjustably (e.g., rotatably) coupled to the lower frame. In one embodiment, upper hinge plate portion 140 is adjustably coupled to lower hinge plate portion 150. In one embodiment, a predetermined range of relative rotational movement is provided. In some embodiments, the rotational positions of the upper frame and the lower frame may be fixed by using one or more fasteners extending through apertures 146, 156. In one embodiment, fasteners 132 extend through circumferential slots 144, 154 to enable relative rotational movement. In other embodiments, or other pivoting features may be provided to enable relative rotational movement of components. In some embodiments, support assembly 110 can selectively provide relative movement or no relative movement dependent on whether the upper and lower frames are fixed in relative position.

Upper liner 114 is received by the upper frame and secured in place using one or more fasteners 122. Upper liner 114 may extend slightly beyond the periphery of cuff portion 136 to minimize contact between cuff portion 136 and a user's arm and to provide a more comfortable fit. Upper liner 114 may be made of a flexible, deformable material such that upper liner 114 conforms to the shape of cuff portion 136. Upper liner 114 (and similarly, lower liner 116) may be made of the same material(s) as upper and lower liners 14,16.

Lower liner 116 includes a strap fastener, a bottom portion 166, and one or more slits. The strap fastener may be similar to strap fastener 40 shown in FIGS. 1-9, and may be configured to couple to lower strap 120 to maintain lower strap 120 in a desired position. The strap fastener may be or include a hook and loop fastener, a mechanical fastener (e.g., a button, clip, threaded fastener, a snap fit fastener, etc.), or any other suitable fastener. In some embodiments lower liner 116 includes one or more slits (e.g., cuts, breaks, etc.), which may be similar to slits 44 shown in FIGS. 1-9. The slits are configured to facilitate placement of support assembly 110 onto a user's arm. The slits may extend longitudinally (e.g., along a length of an arm), transversely, or at other orientations. The slits may form a flap portion that can be flexed to facilitate insertion and removal of a residual limb to and from lower liner 116.

Upper strap 118 is in one embodiment an elongated portion of flexible and/or elastic material configured to wrap about frame assembly 112 and lower liner 114. Upper strap 118 may in some embodiments provide a compressive force to the residual limb. Upper strap 118 may be made of any suitable material, and may include opposite ends that include fasteners such as hook and loop fasteners, etc. Alternatively, strap 118 may be a continuous band of material. Lower strap 120 may be made of the same or similar material and construction, and be configured to wrap about frame assembly 112 and lower liner 116.

Harness assembly 123 includes a shoulder support 170, a shoulder strap 172, and a torso strap 174. As shown in FIG. 11, shoulder support 170 rests on the shoulder of a user adjacent the residual limb. One or more shoulder straps 172 (e.g., front and rear, etc.) couple shoulder support 170 to frame assembly 112 (e.g., to front and rear portions of cuff portion 136 of upper support portion 124). Torso strap 174 extends about the upper back and chest of the user and likewise couples to frame assembly 112 (e.g., to front and rear portions of cuff portion 136 of upper support portion 124). The various straps may be made of elastic material to accommodate movement of the user. In alternative embodiment, a harness similar to harness assembly 22 shown in FIGS. 1-9 may be utilized in connection with support assembly 110. Further, the harness assemblies may be adjustable in length to accommodate variations in users, residual limbs, etc.

In use, support assembly 110 may be provided without straps 118, 120 or harness assembly 123 fully installed (although the components may be loosely attached, e.g., by a single end or in a loosened state). A user places a residual limb (e.g., post BE amputation) within bottom portion 166 of lower liner 116, which forms a lower cup or dome shape to accommodate the distal end of the residual limb. A portion of lower liner 116 may be flexed back dues to various slits to facilitate insertion of the residual limb. Once the residual limb is properly seated within lower liner 116, lower strap 120 may be secured about frame assembly 112 and lower liner 116. Upper strap 118 may be similarly secured about frame assembly 112 and upper liner 114. After straps 118, 120 are properly secured, harness assembly 123 may be positioned and tightened about the torso/chest/back of the user.

In some embodiments, and similar to support assembly 10, support assembly 110 is reversible such that support assembly 110 is usable on either a right or left upper extremity. For example, FIG. 11 illustrates support assembly 110 used with a right residual arm. For use with a left residual arm, harness assembly 123 can be reversed (e.g., by reversing the attachment point and shoulder support positions) and the support assembly 110 can otherwise be fitted as on the left residual arm. Providing a universal support assembly avoids the need to produce different support assemblies to accommodate left and right arms.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be either X, Y, Z; X and Y; X and Z; Y and Z; or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure.

Although the figures and description may illustrate a specific order of method steps, the order of such steps may differ from what is depicted and described, unless specified differently above. Also, two or more steps may be performed concurrently or with partial concurrence, unless specified differently above. All such variations are within the scope of the disclosure.

It is important to note that the construction and arrangement of support assemblies as shown in the various exemplary embodiments is illustrative only. Additionally, any element disclosed in one embodiment may be incorporated or utilized with any other embodiment disclosed herein. For example, the harness assembly of the exemplary embodiment illustrated in at least FIGS. 3-5 and the associated disclosure herein may be incorporated in the support assembly of the exemplary embodiment described in at least FIGS. 10-12. Although only one example of an element from one embodiment that can be incorporated or utilized in another embodiment has been described above, it should be appreciated that other elements of the various embodiments may be incorporated or utilized with any of the other embodiments disclosed herein.

What is claimed is:

1. An upper extremity post-operative support assembly comprising:
   an upper frame;
   a lower frame adjustably coupled to the upper frame;
   a liner coupled to the upper frame and the lower frame, the liner including:
      a first liner portion configured to be positioned adjacent the upper frame and extend at least partially about an arm of a user;
      a second liner portion configured to be positioned adjacent the lower frame, the second liner portion including a closed end configured to receive a distal end of a residual portion of the arm; and
   a body harness coupled with the upper frame and configured to extend about a portion of the body of the user to maintain a desired position of the support assembly.

2. The support assembly of claim 1, further comprising a retention strap configured to extend about the liner and at least one of the upper frame and the lower frame.

3. The support assembly of claim 1, wherein the lower frame is slidably coupled to the upper frame to enable adjustment of an overall length of the support assembly.

4. The support assembly of claim 1, wherein the upper frame and the lower frame are configured to couple to an arm at an above-elbow location.

5. The support assembly of claim 1, wherein the upper frame is rotatably coupled to the lower frame.

6. The support assembly of claim 5, wherein the upper frame includes an upper frame support coupled to an upper hinge portion, wherein the lower frame includes a lower frame support coupled to a lower hinge portion, and wherein the lower hinge portion is rotatably coupled to the upper hinge portion.

7. The support assembly of claim 6, wherein the upper frame support is configured to attach to an arm at an above-elbow location, and wherein the lower frame support is configured to receive the distal end of the residual portion of the arm at a below-elbow location.

8. The support assembly of claim 5, wherein rotation of the upper frame relative to the lower frame accommodates pivoting of an elbow of the arm of the user.

9. The support assembly of claim 1, wherein the first liner portion is coupled to the upper frame and the second liner is separate from the first liner portion and coupled to the lower frame.

10. The support assembly of claim 1, wherein the lower frame and the liner collectively form a protective cavity configured to substantially surround the residual portion of the arm.

11. A post-operative support assembly, comprising:
a frame assembly including an upper cuff portion configured to extend at least partially about an arm, at least one elongated portion configured to extend along a portion of the arm, and a lower cup portion coupled to the upper cuff portion by the at least one elongated portion and configured to extend about a distal end of a residual portion of the arm;
a liner coupled to the frame assembly and positioned between the frame assembly and the residual portion of the arm , the liner configured to at least partially conform to the residual portion of the arm; and
a body harness coupled with the frame assembly and configured to extend about a portion of the body of the user to maintain a desired position of the support assembly.

12. The support assembly of claim 11, wherein the frame assembly includes an upper frame including the upper cuff portion and a lower frame including the lower cup portion, wherein the upper frame is adjustably coupled to the lower frame to enable adjustment of an overall length of the support assembly.

13. The support assembly of claim 11, wherein the lower cup portion is configured to extend about the distal end of the residual portion of the arm at an above-elbow location.

14. The support assembly of claim 11, wherein the lower cup portion is configured to extend about the distal end of the residual portion of the arm at a below-elbow location.

15. The support assembly of claim 11, wherein the liner includes an open top portion and a closed bottom portion forming a dome shape.

16. The support assembly of claim 11, further comprising a retention strap extending about the frame assembly and the liner.

17. A post-operative support assembly comprising:
an upper frame including a curved cuff portion and an upper elongated member;
a lower frame including a curved cup portion and a lower elongated member adjustably coupled to the upper elongated member to enable adjustment of a length between the curved cuff portion and the curved cup portion;
an upper liner coupled to an inner surface of the upper frame;
a lower liner coupled to an inner surface of the lower frame and including an open top portion and a closed bottom portion, wherein the closed bottom portion is dome-shaped and configured to receive a distal end of a residual portion of an arm;
a retention strap extending about the lower frame and the lower liner to secure the lower frame and the lower liner about the residual portion of the arm; and
a body harness coupled with the upper frame and configured to extend about a portion of the body of the user to maintain a desired position of the support assembly.

18. The support assembly of claim 17, wherein the upper frame pivots relative to the lower frame to accommodate pivoting of an elbow of the arm.

19. The support assembly of claim 17, wherein the distal end of the residual portion of the arm is at an above-elbow location.

* * * * *